(12) United States Patent
Patterson et al.

(10) Patent No.: US 7,600,439 B1
(45) Date of Patent: Oct. 13, 2009

(54) APPARATUS AND METHOD FOR STORAGE OF ATMOSPHERIC SAMPLE FOR EVENTUAL CHEMICAL ANALYSIS

(75) Inventors: Garth E. Patterson, Brookston, IN (US); John W. Grossenbacher, Lafayette, IN (US)

(73) Assignee: Griffin Analytical Technologies, Inc., West Lafayette, IN (US)

( * ) Notice: Subject to any disclaimer, the term of this patent is extended or adjusted under 35 U.S.C. 154(b) by 389 days.

(21) Appl. No.: 11/414,195

(22) Filed: May 1, 2006

Related U.S. Application Data (60) Provisional application No. 60/675,896, filed on Apr. 29, 2005.

(51) Int. Cl.
*G01N 1/28* (2006.01)
*G01N 30/62* (2006.01)
*G01N 30/68* (2006.01)
*G01N 30/72* (2006.01)

(52) U.S. Cl. .............. 73/863.21; 73/863.12; 73/863.23; 73/23.37; 73/23.41; 73/31.01

(58) Field of Classification Search .............. 73/863.21, 73/863.12, 863.23–863.31, 863.33, 23.37, 73/23.41, 31.01, 31.02
See application file for complete search history.

(56) References Cited

U.S. PATENT DOCUMENTS

| | | | |
|---|---|---|---|
| 4,546,659 A | 10/1985 | Gill et al. | |
| 5,288,310 A | 2/1994 | Peters et al. | |
| 5,313,061 A * | 5/1994 | Drew et al. .................. | 250/281 |
| 5,402,668 A | 4/1995 | Murakami et al. | |
| 5,551,278 A | 9/1996 | Rounbehler et al. | |
| 5,597,535 A * | 1/1997 | Schaedlich et al. ............ | 422/88 |
| 5,826,577 A | 10/1998 | Perroz, Jr. et al. | |
| 6,477,905 B1 | 11/2002 | Mitra | |
| 6,723,056 B1 | 4/2004 | Alving et al. | |
| 6,819,253 B2 | 11/2004 | Albro et al. | |
| 2008/0229805 A1 * | 9/2008 | Barket et al. ............... | 73/31.01 |

* cited by examiner

*Primary Examiner*—Thomas P Noland
(74) *Attorney, Agent, or Firm*—Finnegan, Henderson, Farabow, Garrett & Dunner, LLP (57) ABSTRACT

The present invention provides a method and system for collecting and storing an atmospheric sample for eventual analysis, where the atmospheric sample includes a mixture of at least a matrix and an analyte. In one implementation, the system includes a housing; a sample cartridge removably attached to the housing, and a pump integrated with the housing and in fluid communication with the sample cartridge, the pump being configured to draw the atmospheric sample through the sample cartridge and to subsequently evacuate the matrix from the sample cartridge. The sample cartridge includes a low thermal mass cylinder with a first end and a second end; an inlet port with a gas-tight inlet valve at the first end of the cylinder, an outlet port with a gas-tight outlet valve at the second end of the cylinder, and a sorbent material disposed within the cylinder and adapted to trap the analyte from the atmospheric sample. In addition, the interior surfaces of the cylinder, inlet valve, and outlet valve upon which sorbent material is not disposed are chemically passive.

16 Claims, 7 Drawing Sheets

APPARATUS AND METHOD FOR STORAGE OF ATMOSPHERIC SAMPLE FOR EVENTUAL CHEMICAL ANALYSIS

CROSS-REFERENCE TO RELATED APPLICATION

This application claims the benefit of U.S. Provisional Application No. 60/675,896, filed Apr. 29, 2005, by John W. Grossenbacher and Garth E. Patterson, and titled APPARATUS AND METHOD FOR STORAGE OF ATMOSPHERIC SAMPLE FOR EVENTUAL CHEMICAL ANALYSIS, the disclosure of which is expressly incorporated herein by reference.

FIELD OF THE INVENTION

The present invention relates to devices for collecting and storing atmospheric samples for eventual chemical analysis.

BACKGROUND OF THE INVENTION

Various devices are known in the art for the collection and storing of atmospheric samples for chemical analysis. For example, U.S. Pat. No. 6,819,253 purports to disclose a system for the collection of near real time confirmation samples to quickly eliminate false positive alarms by confirming the presence of a chemical agent when a monitor operating to detect that chemical agent generates an alarm. The '253 patent allegedly discloses an apparatus that collects air samples on multiple sorbent-filled tubes, which are subsequently heated to drive trapped analytes into a gas chromatograph for chemical analysis. One or more of these tubes may allegedly be preserved for later analysis.

U.S. Pat. No. 6,723,056 purports to disclose a device for storing an air sample, such as exhaled air, in a plastic bag for subsequent off-line determination of the presence of inorganic compounds in the air sample. The '056 patent alleges that the bag may comprise a means to remove or neutralize unwanted matrix components in the samples through the use of reagents or adsorbent materials.

U.S. Pat. No. 6,477,905 purportedly discloses a device and method for continuous on-line or discrete off-line pre-concentration to collect samples of organic compounds in a fluid sample. The '905 patent allegedly discloses an adsorbent trap means, which may comprise a metal tube packed with an adsorbent composition, which traps organic compound contaminants, while allowing matrix gasses such as CO, $CO_2$, $N_2$, $O_2$, $NO_2$, $SO_2$, $CH_4$, and $H_2O$ to pass through. Rapid heating may be used to desorb the trapped analytes for analysis.

U.S. Pat. No. 5,826,577 purports to disclose a breath gas analysis module for collecting and storing a sample of exhaled gas. The '577 patent allegedly discloses an inflatable balloon to store exhaled breath for subsequent analysis with a portable detector, such as for CO exposure.

U.S. Pat. No. 5,551,278 purportedly discloses a system and method for detecting vapors of specific compounds in air. The '278 patent allegedly employs a parallel array of sample tubes in the form of gas chromatography capillary tubing, the interior of which may be coated with methyl silicone or polymerized methyl silicone to adsorb analytes of interest. The matrix air allegedly passes through the capillaries, and the tubes are subsequently heated to desorb the analytes for analysis.

U.S. Pat. No. 5,402,668 purports to disclose a device and apparatus for preconcentrating volatile beer compounds on a porous polymer trap, which is subsequently heated to volatilize the trapped compounds. The '668 patent further alleges that the desorbed compounds are collected again on a cold trap for cryofocusing, in order to sharpen the desorption profile prior to chromatographic analysis.

U.S. Pat. No. 5,288,310 purports to disclose a gas chromatography system in which prefocusing of a sample analyte is provided through the use of an adsorbent coated porous layer open tubular trap tube.

U.S. Pat. No. 4,546,659 purportedly discloses an envelope, or bag, for the collection of atmospheric air samples for subsequent chemical analysis.

As set forth below, the present invention provides an improved system for the collection and storage of analytes from an atmospheric sample.

SUMMARY OF THE INVENTION

Apparatus consistent with one embodiment of the invention provide a system for collecting and storing an atmospheric sample for eventual analysis in which the atmospheric sample includes a mixture of at least a matrix and an analyte. The system includes a housing and a sample cartridge removably attached to the housing. The sample cartridge includes a low thermal mass cylinder with a first end and a second end; an inlet port with a gas-tight inlet valve at the first end of the cylinder; an outlet port with a gas-tight outlet valve at the second end of the cylinder; and a sorbent material disposed within the cylinder and adapted to trap the analyte from the atmospheric sample. The interior surfaces of the cylinder, inlet valve, and outlet valve upon which sorbent material is not disposed are chemically passive. The system also includes a pump integrated with the housing and in fluid communication with the sample cartridge. The pump is configured to draw the atmospheric sample through the sample cartridge and to subsequently evacuate the matrix from the sample cartridge.

Apparatus consistent with another embodiment of the invention provide a system for collecting and storing at least two atmospheric samples for eventual analysis in which the atmospheric samples include a mixture of at least a matrix and an analyte. The system includes a housing and at least two sample cartridges removably attached to the housing. Each sample cartridge includes a low thermal mass cylinder with a first end and a second end; an inlet port with a gas-tight inlet valve at the first end of the cylinder; an outlet port with a gas-tight outlet valve at the second end of the cylinder; and a sorbent material disposed within the cylinder and adapted to trap the analyte from the atmospheric sample. The interior surfaces of the cylinder, inlet valve, and outlet valve upon which sorbent material is not disposed are chemically passive. The system also includes a pump integrated with the housing and in fluid communication with the at least two sample cartridges. The pump is configured to draw one of the at least two atmospheric samples through one of the at least two sample cartridges and to subsequently evacuate the matrix from each sample cartridge. The system further includes a valve in fluid communication with the at least two sample cartridges to selectively direct each atmospheric samples into a selected sample cartridge.

Methods consistent with another embodiment of the invention provide a method of collecting and storing analytes from an atmospheric sample for eventual analysis in which the atmospheric sample includes a mixture of at least an analyte and a matrix. The method includes providing a housing and removably attaching a sample cartridge to the housing. The sample cartridge includes a low thermal mass cylinder with a first end and a second end; an inlet port with a gas-tight inlet valve at the first end of the cylinder; an outlet port with a gas-tight outlet valve at the second end of the cylinder, and a sorbent material disposed within the cylinder and adapted to trap the analyte from the atmospheric sample. The interior surfaces of the cylinder, inlet valve, and outlet valve upon which sorbent material is not disposed are chemically passive. The method further includes integrating a pump with the housing in fluid communication with the sample cartridge; activating the pump with each of the inlet valve and the outlet valve both in an open position to draw the atmospheric sample through the sample cartridge and trap the analyte within the sorbent material; closing the inlet valve while the pump is activated to evacuate the matrix from the sample cartridge; and closing the outlet valve to isolate the analyte within the sample cartridge for storage.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

Figure 1A:
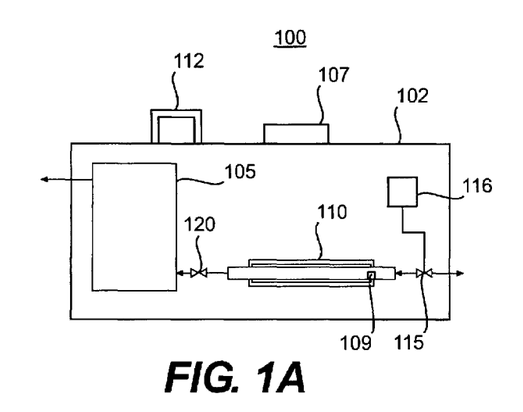
FIG. 1A illustrates a sample collection system for collecting and storing analytes borne by an atmospheric sample consistent with one embodiment of the invention.

FIG. 1A illustrates a sample collection system for collecting and storing analytes borne by an atmospheric sample consistent with one embodiment of the invention. As shown in FIG. 1A, in one implementation, sample collection system 100 includes a sample cartridge 110, an inlet valve 115 and an outlet valve 120 in fluid communication with sample cartridge 110, and a pump 105 in fluid communication with sample cartridge 110. These components are contained in a housing 102. A sample flow path is defined by the path the atmospheric sample follows as it is drawn through inlet valve 115 into sample cartridge 120, through outlet valve 120, and through pump 105.

Sample cartridge 110 is configured to trap analytes borne by an atmospheric sample passed through the sample cartridge. Examples of sample cartridges consistent with embodiments of the invention are described in detail below. Pump 105 may be any pump suitable for drawing an atmospheric sample through sample cartridge 110. As explained below, pump 105 may also be used to evacuate sample cartridge 110 after sample collection. Inlet valve 115 and outlet valve 120 may be any valves of the type typically used in sample collection systems. In addition, valves 115 and 120 may be integrated in sample cartridge 110 or may be separate components. In another implementation, a flowmeter 109 may be disposed a point along the sample flow path to measure the flow rate of the atmospheric sample through the system 100. These implementations are merely exemplary, and other implementations may also be used.

Generally, in order to collect analytes using sample collection system 100, valves 115 and 120 are opened enabling pump 105 to draw an atmospheric sample through sample cartridge 110. Analytes from the atmospheric sample are trapped in sample cartridge 110 as the sample is passed through sample cartridge 110. The atmospheric samples collected by the present invention may comprise a matrix, such as, e.g., atmospheric gases, including oxygen and nitrogen, that contain materials to be analyzed. The matrix may also be in the liquid phase. The materials to be analyzed may include potentially harmful chemical contaminants or pollutants, such as toxic industrial chemicals; biological materials, such as anthrax spores; chemical warfare agents, such as sarin; and radioisotopes. These materials are selectively removed from the atmospheric sample for later analysis.

In one implementation, a sample collection system, such as sample collection system 100, may also include a housing 102 configured to carry sample cartridge 110, pump 105, and valves 115 and 120. In this implementation, sample cartridge 110 may be configured so as to be removably securable within the housing. For example, sample cartridge 110 may be removably connected in fluid communication with pump 105 via an outlet port on sample cartridge 110. Alternatively, sample cartridge 110 may be removably connected directly to the pump.

The dimensions of housing 102 and the weight of the components carried thereon may be such that the system can be hand-held or otherwise portable. As shown in FIG. 1A, housing 102 may include a handle 112. Alternatively, or additionally, the system may be constructed to be easily carried, for example, on a user's back, or over a user's shoulder. Sample cartridge 110 may alternatively be used in conjunction with the hand-held sampler disclosed in PCT patent application No. PCT/US05/43953, which claims priority from U.S. Provisional Application No. 60/633,725, both of which are incorporated herein by reference. In one implementation where sample cartridge 110 is removably securable within the housing, sample cartridge 110 is relatively lightweight and portable. In this implementation, a user may easily take several samples from a single site or from a plurality of sites, while keeping both used and un-used sample cartridges on his person. These implementations are merely exemplary, and other implementations may also be used.

Figure 6:
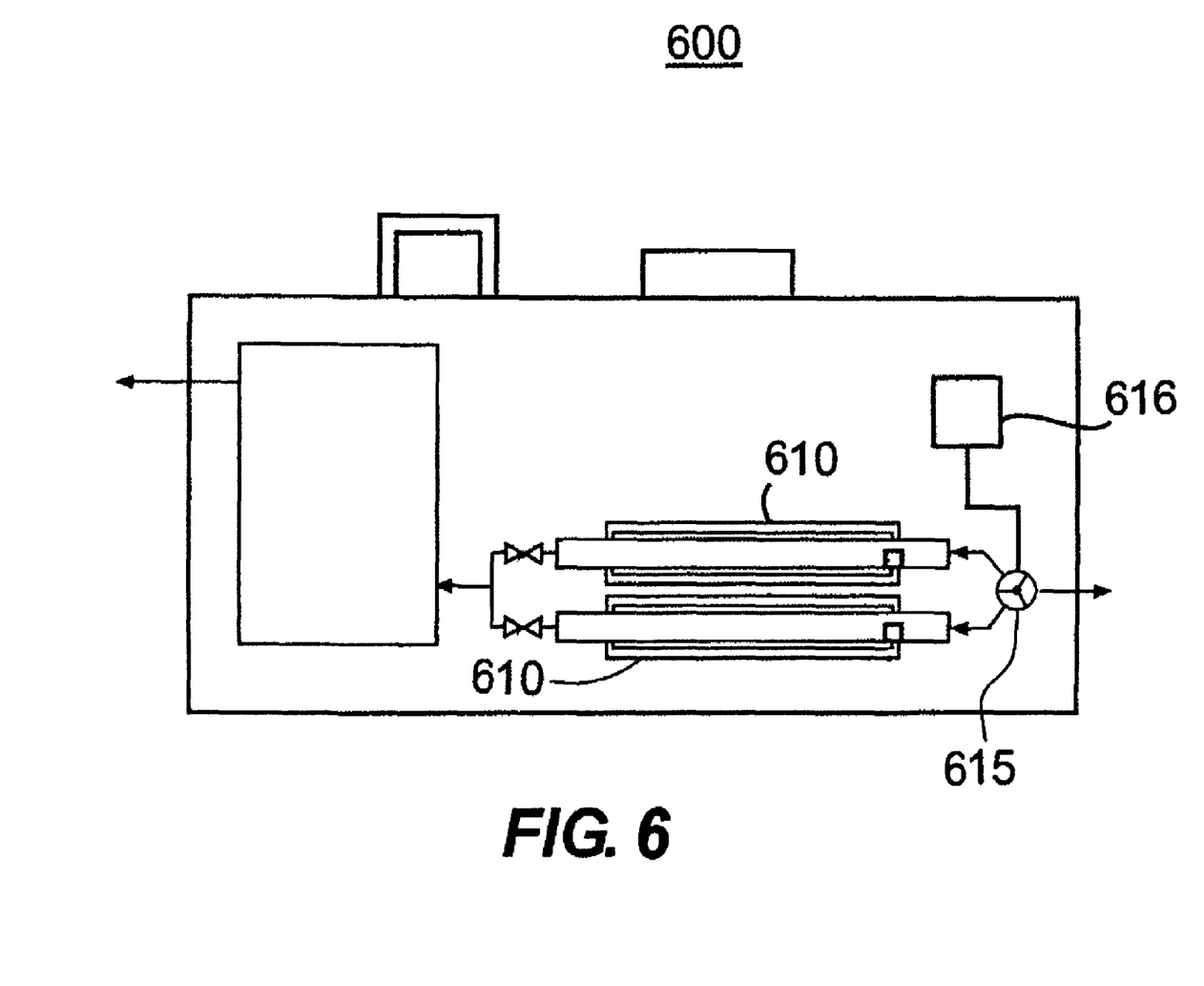
FIG. 6 illustrates a sample collection system for collecting and storing analytes borne by an atmospheric sample within multiple cartridges consistent with one embodiment of the invention.

In another implementation, as shown in FIG. 6, a sample collection system 600 may also have the capability to collect multiple discrete analyte samples. In this implementation, the housing will carry multiple sample cartridges 610 removably secured thereto. The housing may further include a multi-port valve 615 and/or a series of valves to selectively direct the sample flow path through a first sample cartridge by fluidly connecting the outlet port of the first sample cartridge with the pump 616. Once a first analyte sample is trapped within the first sample cartridge, the inlet valve and outlet valve within the first sample cartridge may be closed to isolate the analyte sample within the cylinder of the first sample cartridge. The multi-port valve 615 and/or series of valves may then be engaged to selectively direct the sample flow path through a second sample cartridge in order to collect and store a second, discrete, analyte sample within the housing. This process may be repeated for each subsequent sample cartridge carried by the housing. To prevent contamination of each sample cartridge both prior to and after sample collection, the inlet valve and outlet valve of each sample cartridge may be in a closed position when not in fluid communication with the pump. This implementation is merely exemplary, and other implementations may also be used.

Once pump 105 has drawn the atmospheric sample through sample cartridge 110 for a time sufficient to adsorb a given amount of analyte, sample collection system 100 may evacuate the matrix portion of the atmospheric sample from sample cartridge 110. Sample cartridge 110 may be effectively evacuated by closing inlet valve 115 while pump 105 is activated. In order to effectively evacuate sample cartridge 110, pump 105 may be capable of generating a low vacuum within sample cartridge 110. In one implementation, pump 105 may be capable of generating a vacuum of, for example, less than 1 Torr.

In one implementation, once pump 105 has evacuated sample cartridge 110, the analyte may be sealed within sample cartridge 110 by closing outlet valve 120. Pump 105 may then be de-activated. With the analytes so isolated within the reduced pressure of sample cartridge 110, the analytes may be preserved without degradation for a longer period than if sealed within sample cartridge 110 with the matrix present. By evacuating the cylinder prior to storage, reaction with other species within the sample matrix that may be present at orders of magnitude greater concentrations, including, e.g., water, ozone, and $O_2$ is prevented. With the analytes preserved within the near vacuum of the cylinder, the analytes may have a shelf-life of, for example, up to approximately three months. During this shelf life, the analytes may remain fully reversibly sequestered, and may be fully desorbed from sample cartridge 110 when tested. This extended shelf life may be necessary due to the prevalence of back-logs in analytical chemical labs. This implementation is merely exemplary, and other implementations may also be used.

In one implementation, analyte sample preservation may be further optimized by passivating, i.e., making less reactive, all interior surfaces of sample cartridge 110 that may contact the atmospheric sample and the analyte carried therein. Passivating those surfaces may effectively eliminate chemical consumption of the analyte through reaction at active sites on sample cartridge 110. This implementation is merely exemplary, and other implementations may also be used.

In another implementation, the method of storing the analytes within sample cartridge 110 may further entail introducing a volume of inert gas such as, e.g., helium or argon, into the sample cartridge 110 after evacuation. As shown in FIG. 1A, a source of inert gas 116 may be fluidly coupled with, for example, inlet valve 115 of sample cartridge 110, while outlet valve 120 remains closed. With a near vacuum already established within sample cartridge 110, a volume of the inert gas will flow into sample cartridge 110. Once a given volume of the inert gas is present within sample cartridge 110, inlet valve 115 may be closed, thereby isolating the analyte and the inert gas. In this implementation, the presence of the inert gas may further preserve the trapped analytes. This implementation is merely exemplary, and other implementations may also be used.

In another implementation, the method of storing the analyte may further entail un-coupling sample cartridge 110 from the pump and/or housing. Once un-coupled, sample cartridge 110 may then be stored for the duration of its effective shelf-life prior to analyzing the analyte trapped therein. Sample cartridge 110 may be coupled to pump 105 and/or housing conventional standard fittings. Conventional quick-connect fittings that require no tools to secure and break the fluid connections may be used, which may be advantageous for in-field use. Further, the fittings may include automatic shutoffs, in which a plunger closes a valve to prevent leakage or contamination if the connection is broken. The fittings may be constructed of a durable material for repeated use such as, e.g., stainless steel. To further prevent degradation of the sample, the fittings may include passivated surfaces. These fittings are well-known to those skilled in the art, and are commercially available from, e.g., Swagelok® and Parker. The fittings may also include manual shut-off valves disposed along the sample flow path which may be operable by a user wearing personal protective equipment (PPE), which may be common when taking atmospheric samples from a site suspected of containing, for example, toxic industrial chemicals or hazardous biological materials. This implementation is merely exemplary, and other implementations may also be used.

Figure 1B:
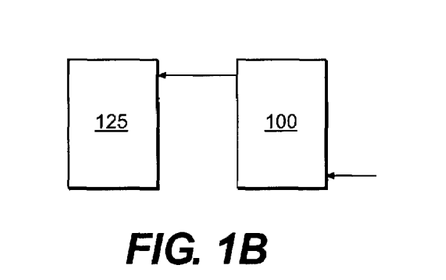
FIG. 1B illustrates a sample collection system in fluid communication with a chemical analyzer consistent with one embodiment of the invention.
Figure 1C:
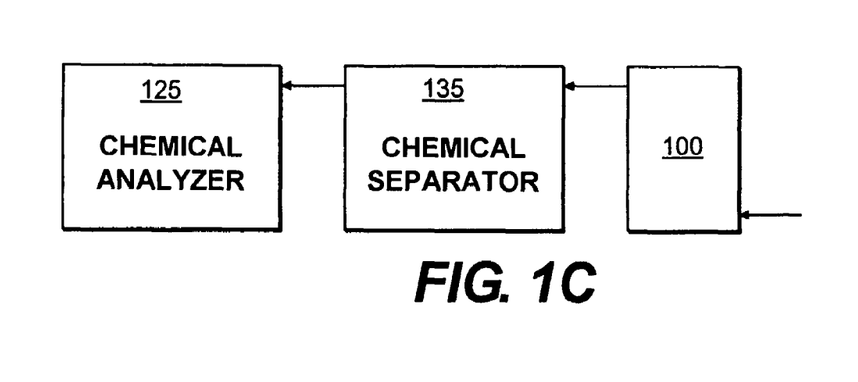
FIG. 1C illustrates a sample collection system in fluid communication with a chemical separator and a chemical analyzer consistent with one embodiment of the invention.

The method of the present invention may also entail flushing the trapped analyte from sample cartridge 110 after storage. In order to test for a given analyte, sample cartridge 110 containing a trapped analyte may be fluidly coupled to the input of a chemical analyzer, such as a flame ionization detector, a nitrogen phosphorous detector, a flame photometric detector, a mass spectrometer, a portable mass spectrometer, or a portable cylindrical ion trap mass spectrometer, a chemical separator, such as a gas chromatograph, or a combination chemical analyzer/chemical separator, such as, a gas chromatograph, a gas chromatograph/flame ionization detector, a gas chromatograph/nitrogen phosphorous detector, a gas chromatograph/flame photometric detector, a gas chromatograph/mass spectrometer, a portable mass spectrometer, or portable cylindrical ion trap mass spectrometer. FIG. 1B illustrates a sample collection system 100 in fluid communication with a chemical analyzer 125 consistent with one embodiment of the invention and FIG. 1C illustrates a sample collection system 100 in fluid communication with a chemical separator 135 and a chemical analyzer 125 consistent with one embodiment of the invention.

Once coupled to analyzer device, the analyte trapped within sample cartridge 110 may be flushed from sample cartridge 110 into the analytical device by opening each of inlet valve 115 and outlet valve 120 and flowing an inert carrier gas such as, e.g., helium or argon, through the sample cartridge. The carrier gas may be drawn through sample cartridge 110 by the same pump 105 described above, while fluidly connected to both the outlet port of sample cartridge 110 and the input of the analytical device. Alternatively, the carrier gas may be drawn through sample cartridge 110 by a second pump, which may be free-standing or integrated with the analytical device. To more efficiently desorb the trapped analyte from the sorbent material, the heating element described above may be activated so as to volatilize the analytes. These implementations are merely exemplary, and other implementations may also be used.

In another implementation, sample collection system 100 may further comprise a programmable control unit 107 for controlling the operation of the system. Control unit 107 may be carried upon sample cartridge 110 itself, or be integrated with the housing. Control unit 107 may include a memory unit that carries operation instructions. These operation instructions may automatically control the operation of, and interaction between, e.g., inlet valve 115 and output valve 120, the pump 105, and any sensors disposed on the system for that purpose. The action of sample collection system 100 may be triggered by the presence of analyte in the atmospheric sample. For example, if the system is operated in conjunction with a mass spectrometer or other such chemical detection device that monitors levels of analyte such as total hydrocarbon loading above a threshold, the system can be operated in order to obtain a sample for later analysis including confirmatory analysis. For example, control unit 107 may place input valve 115 and output valve 120 in an open position in order to collect an atmospheric sample. Control unit 107 may then activate the pump at a power sufficient to induce turbulent flow within the cylinder of sample cartridge 110. Control unit 107 may operate pump 105 for a predetermined time threshold. Alternatively, control unit 107 may sample the output of, for example, a flowmeter, and operate pump 105 until a predetermined threshold volume has flowed through the system. When the threshold parameter is reached, control 107 unit may then effect evacuation of sample cartridge 110 by closing input valve 115 while continuing to operate pump 105. The control unit may then sample the output of one or more of, for example, a pressure, $O_2$, or moisture sensor within sample cartridge 110 to determine if an evacuation threshold has been met. Once the evacuation threshold has been met, the control unit may de-activate pump 105 and close output valve 120 in order to isolate the trapped analyte within the cylinder of sample cartridge 110. Alternatively, the operation of each component of the present invention, including, e.g., pump 105, inlet valve 115, and outlet valve 120 may be manually operated. These implementations are merely exemplary, and other implementations may also be used.

Figure 2:
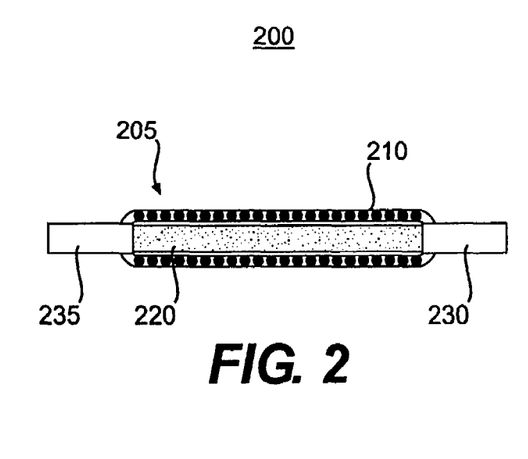
FIG. 2 is a longitudinal cross-sectional view of a sample cartridge consistent with one embodiment of the invention.

As described above, sample cartridge 110 is designed to trap analytes from an atmospheric sample. FIGS. 2-5 illustrate different embodiments of sample cartridges consistent with the invention. FIG. 2 is a longitudinal cross-sectional view of a sample cartridge 200 consistent with one embodiment of the invention. Sample cartridge 200 is arranged to trap a sample of analytes borne by the volume of atmospheric gas as it passes through sample cartridge 200, as discussed above. The analytes trapped by sample cartridge 200 may be eventually tested in a chemical analyzer, as discussed above.

As shown in FIG. 2, sample cartridge 200 comprises a cylinder 205 with an inlet port 230 at a first end of cylinder 205 and an outlet port 235 at a second end of cylinder 205, inlet port 230 and outlet port 235 being configured to allow an atmospheric sample to flow through the interior of cylinder 205. Inlet port 230 may be in fluid communication with the open atmosphere to be sampled, while outlet port 235 may be in fluid communication with a pump, such as pump 105 described above. Sample cartridge 200 may further include means to hermetically seal cylinder 205, thereby isolating the analytes trapped therein from the atmosphere and preventing contamination of cylinder 205. Hermetically sealing cylinder 205 prior to taking the atmospheric sample also serves to prevent contamination of cylinder 205. In one implementation, cylinder 205 is sealed by employing an inlet valve and an outlet valve located at the first and second ends of cylinder 205, respectively. The inlet and outlet valves may be manually or electrically actuated, and examples of appropriate valves are well-known to those skilled in the art. In another implementation, the present invention may further include an additional filter disposed at a point upstream of sample cartridge 220 to filter debris and other solid or liquid particulates as desired. Such filters are well-known in the art. These implementations are merely exemplary, and other implementations may also be used.

As shown in FIG. 2, sample cartridge 200 includes a sorbent material 220 disposed within cylinder 205. In this implementation, sorbent material 220 removes analytes from an atmospheric sample as the atmospheric sample flows over, or through, sorbent material 220. In the implementation of FIG. 2, cylinder 205 is substantially filled with solid sorbent material 220, with sufficient interconnected interstices within sorbent material 220 to allow the atmospheric sample to flow through the bulk sorbent material and around, over, and/or through the individual sorbent particles. This implementation is merely exemplary, and other implementations may also be used.

Sorbent material 220 may be any material suitable to trap through adsorption specific analytes borne by the atmospheric sample as the atmospheric sample is drawn through sample cartridge 200. A user of the present invention may choose an appropriate sorbent material based upon the particular analytes sought to be selectively removed from an atmospheric sample for analysis. One skilled in the art would easily recognize which sorbent materials are most effective for a given use. In one implementation, sorbent material 220 may be, for example, in a granular form. Such granular sorbent materials include Temax™ and Chromosorb™. Microporous filters that employ, for example, Teflon™ or Nylon™ fibers, as well as solid phase microextraction (SPME) fibers may also be used to selectively adsorb analytes from an atmospheric sample. Other readily-available commercial products are well-known to those skilled in the art. These implementations are merely exemplary, and other implementations may also be used.

As shown in FIG. 2, in this implementation, cylinder 205 may also include a heating element 210 to facilitate desorption of the trapped analytes for analysis. Once activated, heating element 210 volatilizes the trapped analytes, making the process of flushing the analytes from sorbent material 220 more efficient. This heating procedure is well-known to those skilled in the art, and heat has been typically used to release trapped analytes in, e.g., various membrane introduction mass spectrometry (MIMS) techniques, specifically single-sided MIMS and trap-and-release MIMS. As shown in FIG. 2, heating element 210 may be integrated with at least a portion of the circumference of cylinder 205 along the length of cylinder 205. Such an integrated heating element is commercially available from ThermoCoax. In another implementation, a heating element is not integrated with cylinder 205. Rather, at least one external heater is provided in order to heat the cylinder during desorption. These external heaters may be relatively low-power (10-50 W) heaters of the cartridge type. Alternative means of heating the sample cartridge in order to effect desorption of the analyte are well-known to those skilled in the art. In addition, sample cartridge 200, including the cylinder 205, may be constructed of a material such as, e.g., aluminum, having good thermal conductivity, and may have a low thermal mass. Such materials may efficiently transfer heat from the heating element to the sorbent material. Materials such as aluminum are also sufficiently lightweight and rugged for in-field applications. These implementations are merely exemplary, and other implementations may also be used.

In another implementation, the interior of all surfaces of cylinder 205 that are not otherwise coated or lined with sorbent material 220 (i.e., all surfaces that are potentially exposed to analytes as the atmospheric sample flows through the sample cartridge) may be chemically treated, or passivated, to eliminate the likelihood of irreversible sample loss through chemical destruction on non-membrane surfaces or permanent desorption thereto. Such passivation techniques are common to gas chromatograph systems and are well-known in the art. Commercially available passivation treatments to effect a non-reactive surface include, e.g., Siltek™, Sulfinert™, Silcosteel™ (all available from Restek Corp.), and Teflon™. This implementation is merely exemplary, and other implementations may also be used.

Figure 3:
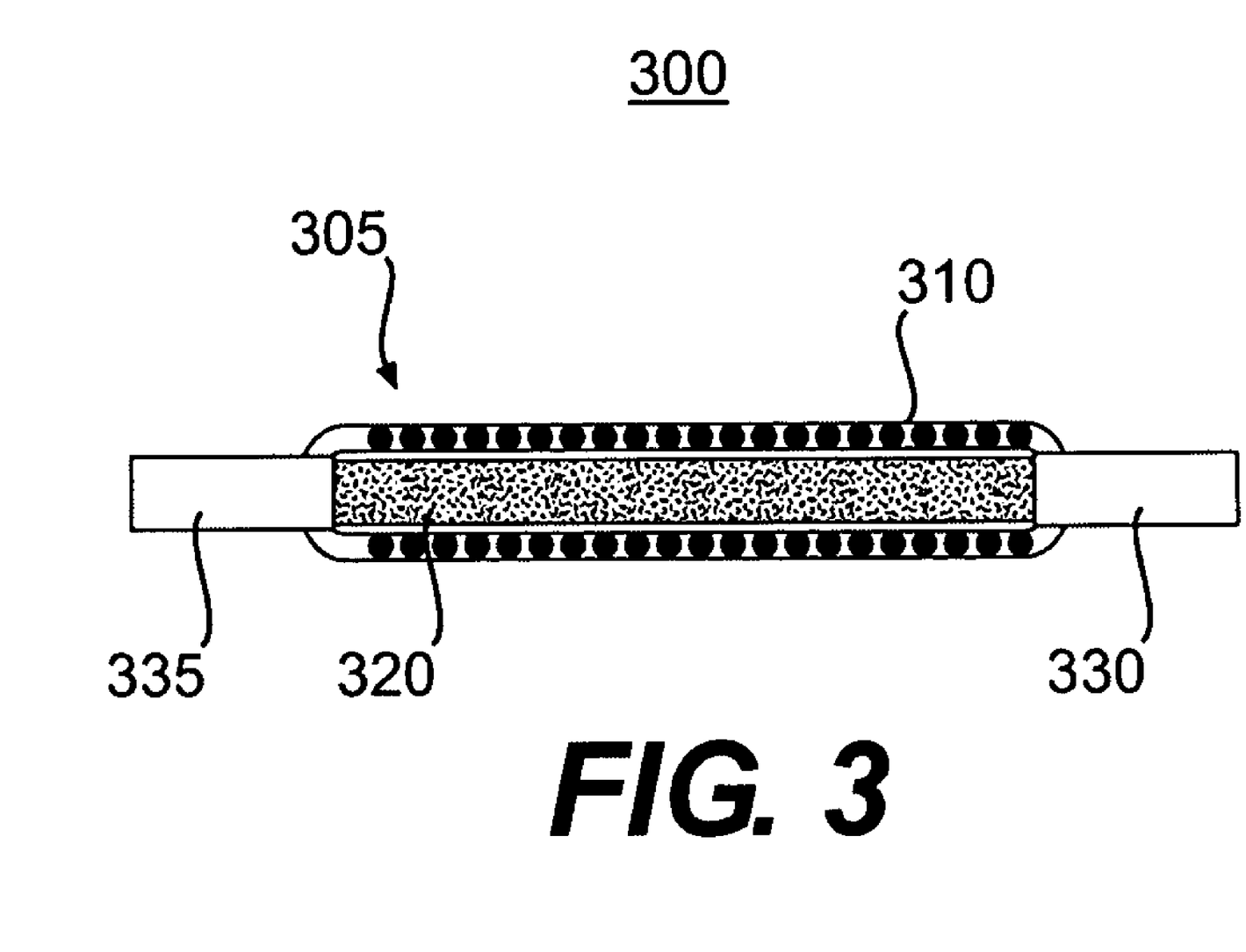
FIG. 3 is a longitudinal cross-sectional view of a sample cartridge consistent with another embodiment of the invention.

FIG. 3 is a longitudinal cross-sectional view of a sample cartridge consistent with another embodiment of the invention. As shown in FIG. 3, sample cartridge 300 includes a cylinder 305, an inlet port 330, an outlet port 335, integral heater 310, and a sorbent material 320, similar to sample cartridge 200 of FIG. 2. In this implementation, however, sorbent material 320 comprises a semi-permeable membrane material lining the interior surface of the cylinder. The membrane material may be similar to that used in membrane introduction mass spectrometry (MIMS), a proven means of selectively removing analytes from an atmospheric sample for analysis. As with applications employing the MIMS process, the membrane coating may comprise, for example, polymerized methyl silicone (PDMS). The mass of the membrane lining may determine the amount of analyte that may be trapped therein, while the thickness of the membrane coating may at least partly determine the length of time necessary for desorption. One skilled in the art would readily recognize appropriate membranes that may be used with the present invention to trap analytes. This implementation is merely exemplary, and other implementations may also be used.

In one implementation, the inside diameter of the membrane-lined cylinder 305 may be dimensioned to provide a maximum surface area on which to trap analytes from an atmospheric sample. With sufficient flow rate through cylinder 305, turbulent flow will efficiently bring the analytes into contact with the membrane 320. This implementation is merely exemplary, and other implementations may also be used.

Figure 4A:
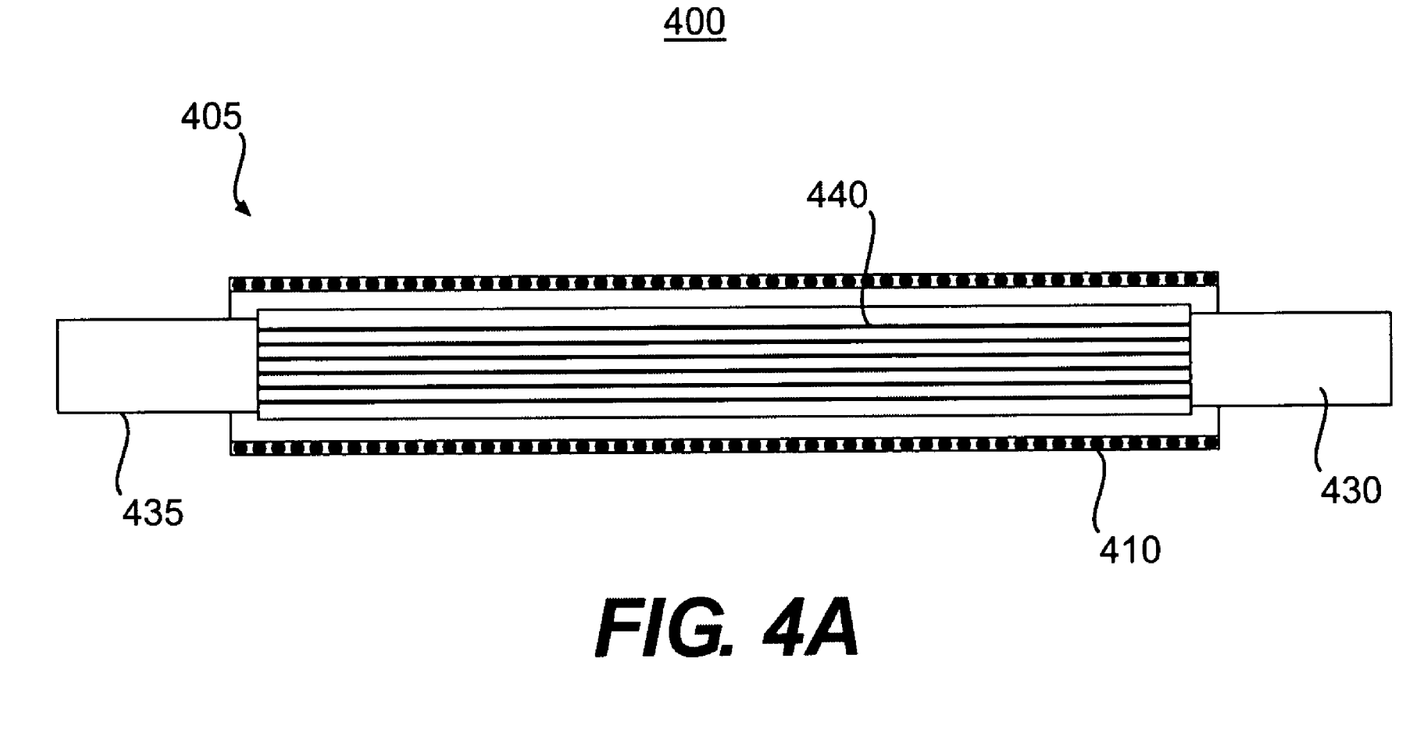
FIG. 4A is a cross-sectional view of a sample cartridge consistent with another embodiment of the invention.
Figure 4B:
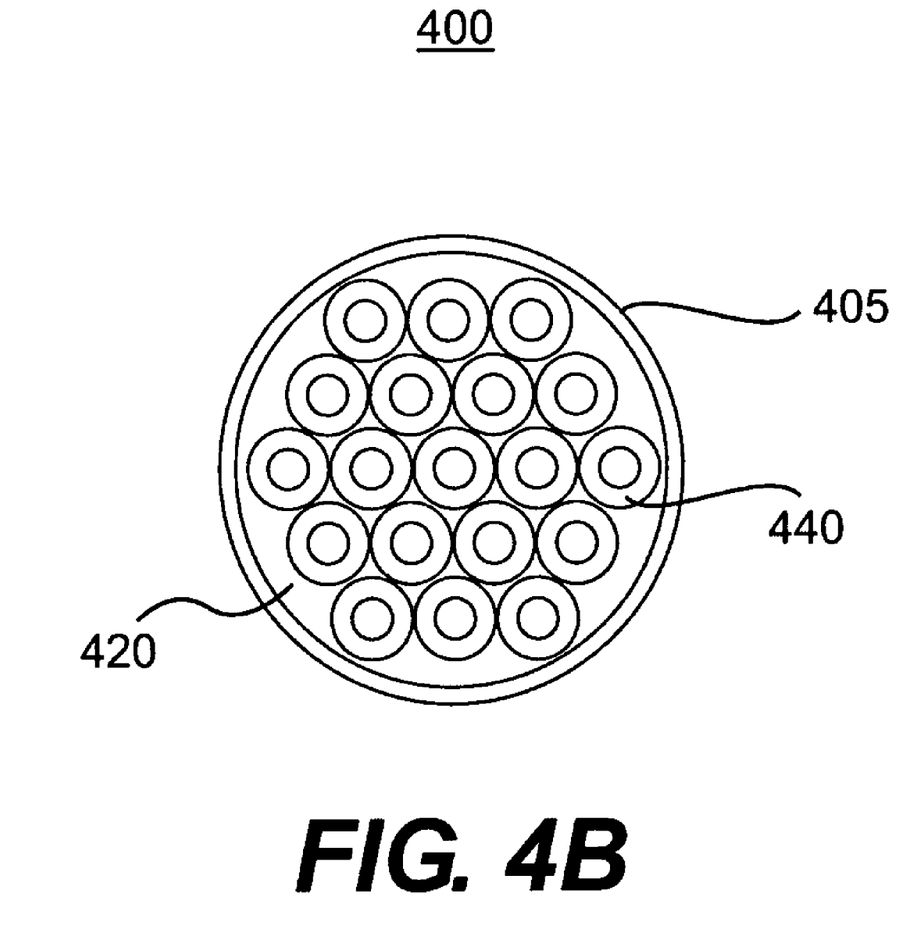
FIG. 4B is a side view of a sample cartridge consistent with the embodiment of the invention as shown in FIG. 4A.

FIGS. 4A-4B are two views of a sample cartridge consistent with another embodiment of the invention. As shown in FIGS. 4A-4B, sample cartridge 400 includes a cylinder 405, an inlet port 430, an outlet port 435, and an integral heater 410, similar to sample cartridge 300 of FIG. 3. Sample cartridge 400 also includes a sorbent material (not shown) comprising a semi-permeable membrane material lining the interior surface cylinder 405, similar to sample cartridge 300 of FIG. 3. In this implementation, to optimize the surface area on which to trap analytes, a plurality of substantially parallel tubes 440 are disposed within cylinder 405. Each of parallel tubes 440 is in fluid communication with inlet port 430 and outlet port 435 of cylinder 405 through which the atmospheric sample is pumped. The parallel tubes may range in size from an outside diameter of, for example, less than one millimeter, up to 3.2 mm. Tubes within this range are readily available, and commercially produced by suppliers such as Fisher Scientific. In this implementation, the interior of parallel tubes 440 will also include sorbent material. This sorbent material may be any sorbent material for trapping an analyte, including, but not limited to, a granular material as discussed with respect to FIG. 2 or a membrane material as discussed with respect to FIG. 3. This implementation is merely exemplary, and other implementations may also be used.

Figure 5:
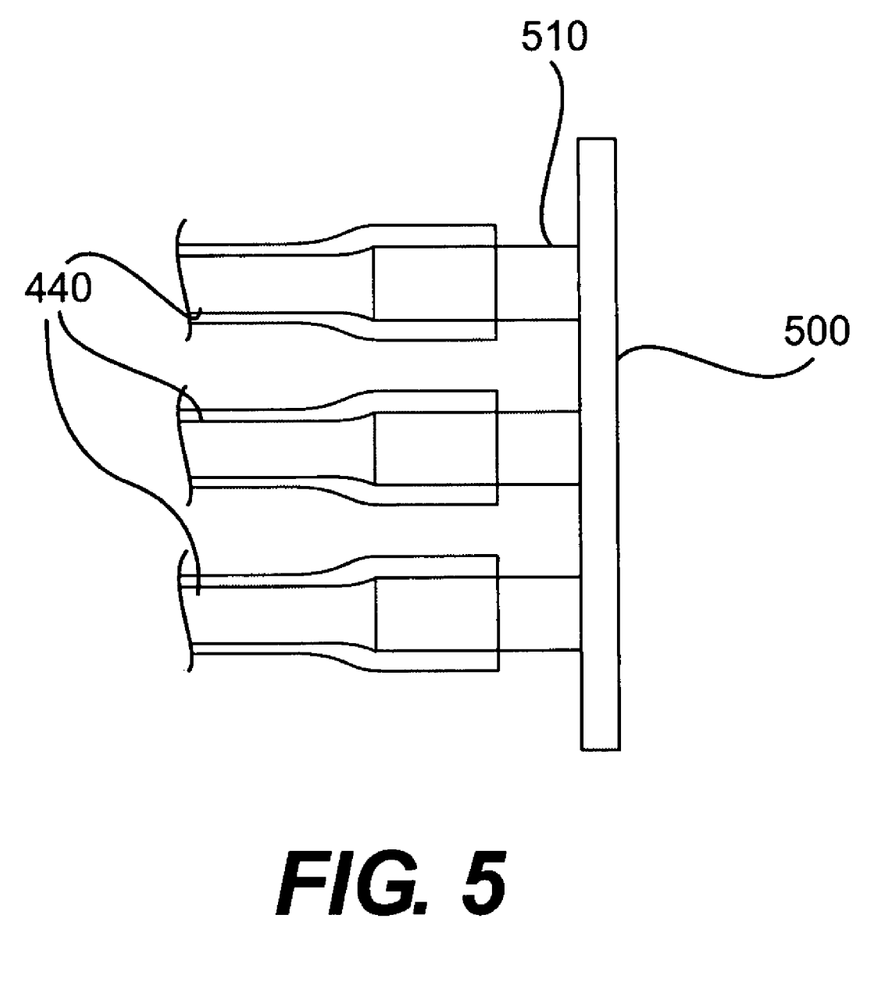
FIG. 5 is a side view of a plate to secure parallel tubes in a sample cartridge consistent with one embodiment of the invention, as shown in FIGS. 4A-4B.

In one implementation, sample cartridge 400 will include plates designed to secure parallel tubes 440 within cylinder 405. FIG. 5 is a side view of a plate to secure parallel tubes in a sample cartridge consistent with one embodiment of the invention, as shown in FIGS. 4A-4B. In this implementation, at each end of cylinder 405, a plate 500 may be inserted to secure parallel tubes 440 within cylinder 405. As shown in FIG. 5, each plate 400 includes a plurality of fittings 510, to which each respective parallel tube 440 is secured and through which an atmospheric sample may flow. In one implementation, each fitting may comprise a cylindrical "male" fitting, over which a respective parallel tube 440 (the "female" fitting) may be secured, or vice versa. Each of these fittings has a corresponding opening on plate 400 through with an atmospheric sample can be drawn through a fitting and into a parallel tube. This implementation is merely exemplary, and other implementations may also be used.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for collecting and storing an atmospheric sample for eventual analysis, the atmospheric sample comprising a mixture of at least a matrix and an analyte, the system comprising:
   a housing;
   a sample cartridge removably attached to the housing, the sample cartridge comprising:
      a low thermal mass cylinder with a first end and a second end;
      an inlet port with a gas-tight inlet valve at the first end of the cylinder;
      an outlet port with a gas-tight outlet valve at the second end of the cylinder; and
      a sorbent material disposed within the cylinder and adapted to trap the analyte from the atmospheric sample;
      wherein interior surfaces of the cylinder, inlet valve, and outlet valve upon which sorbent material is not disposed are chemically passive;
   a pump integrated with the housing and in fluid communication with the sample cartridge, the pump being configured to draw the atmospheric sample through the sample cartridge and to subsequently evacuate the matrix from the sample cartridge.

2. The system of claim 1, wherein the housing is configured to be carried by a single person.

3. The system of claim 1, wherein the sample cartridge further comprises a plurality of parallel tubes disposed within the sample cartridge, each of the plurality of parallel tubes being in fluid communication with the inlet port and the outlet port, the sorbent material being disposed within each of the plurality of parallel tubes.

4. The system of claim 1, wherein the chemical sample cartridge further comprises a heating element to facilitate desorption of the trapped analyte.

5. The system of claim 1, further comprising a chemical analyzer in fluid communication with the sample cartridge.

6. The system of claim 5, wherein the chemical analyzer is a mass spectrometer, a portable mass spectrometer, a portable cylindrical ion trap-mass spectrometer, a flame ionization detector, a nitrogen-phosphorous detector, or a flame photometric detector.

7. The system of claim 5, further comprising a programmable control unit to control operation of the inlet valve, outlet valve, pump, and chemical analyzer.

8. The system of claim 1, further comprising a chemical separator in fluid communication with the sample cartridge.

9. The system of claim 8, wherein the chemical separator is a gas chromatograph.

10. The system of claim 1, further comprising a combination chemical separator and chemical analyzer in fluid communication with the sample cartridge.

11. The system of claim 10, wherein the combination chemical separator/chemical analyzer is a gas chromatograph/flame ionization detector, a gas chromatograph/nitrogen-phosphorous detector, a gas chromatograph/flame photometric detector, or a gas chromatograph/mass spectrometer.

12. The system of claim 1, wherein the sampling system includes at least one sensor within the sample cartridge to determine the presence of an atmospheric sample.

13. The system of claim 1, further comprising a source of inert gas, wherein the source of inert gas is in fluid communication with the sample cartridge, and the pump is configured to draw a volume of inert gas into the evacuated sample cartridge for storage.

14. The system of claim 1, wherein the sorbent material comprises a granular sorbent material.

15. The system of claim 1, wherein the sorbent material comprises a semi-permeable membrane material.

16. A system for collecting and storing at least two atmospheric samples for eventual analysis, the atmospheric samples comprising a mixture of at least a matrix and an analyte, the system comprising:
- a housing;
- at least two sample cartridges removably attached to the housing, each sample cartridge comprising:
  - a low thermal mass cylinder with a first end and a second end;
  - an inlet port with a gas-tight inlet valve at the first end of the cylinder;
  - an outlet port with a gas-tight outlet valve at the second end of the cylinder; and
  - a sorbent material disposed within the cylinder and adapted to trap the analyte from the atmospheric sample;
  - wherein interior surfaces of the cylinder, inlet valve, and outlet valve upon which sorbent material is not disposed are chemically passive;
- a pump integrated with the housing and in fluid communication with the at least two sample cartridges, the pump being configured to draw one of the at least two atmospheric samples through one of the at least two sample cartridges and to subsequently evacuate the matrix from each sample cartridge; and
- a valve in fluid communication with the at least two sample cartridges to selectively direct each atmospheric sample into a selected sample cartridge.

* * * * *